United States Patent [19]
Kadhiresan

[11] Patent Number: 5,935,081
[45] Date of Patent: Aug. 10, 1999

[54] LONG TERM MONITORING OF ACCELERATION SIGNALS FOR OPTIMIZATION OF PACING THERAPY

[75] Inventor: V. A. Kadhiresan, Lino Lakes, Minn.

[73] Assignee: Cardiac Pacemakers, Inc., St. Paul, Minn.

[21] Appl. No.: 09/009,424

[22] Filed: Jan. 20, 1998

[51] Int. Cl.[6] .................................................. A61B 5/0402
[52] U.S. Cl. ........................................... 600/513; 600/514
[58] Field of Search ................................... 600/509, 513, 600/514

[56] References Cited

PUBLICATIONS

"Accelerometer Type Cardiac Transducer for Detection of Low–Level Heart Sounds" by Padmanabhan et al., *IEE Trans Biomed Eng.*, Jan. 1993; 40(1):21–28.

Walsh JT et al., "Relation of Daily Activity Levels in Patients With Chronic Heart Failure to Long–Term Prognosis", *Am J. Cardiol*, May 15, 1997;79(10):1364–1369.

Hanly PJ, Zuberi–Khokhar NS "Increased Mortality Associated with Cheyne–Stokes Respiration in Patients With Congestive Heart Failure", *Am. J. Respir Crit Care Med*, Jan. 1996; 153(1):272–276.

Manson AL et al., "Relationship of the Third Heart Sound to Transmitral Flow Velocity Deceleration", *Circulation* Aug. 1, 1995;92(3):388–394.).

Kono T et al., "Hemodynamic Correlates of the Third Heart Sound During the Evolution of Chronic Heart Failure" *J Am Coll Cardiol* Feb. 21, 1993(2):419–423.).

Patel R. et al, "Implications of an Audible Third Heart Sound in Evaluating Cardiac Function", *West J Med* Jun. 1993;158(6):606–609.

Pinamonti B et al, "Restrictive Left Ventricular Filling Pattern in Dilated Cardiomyopathy Assessed by Doppler Echocardiography: Clinical, Echocardiographic and Hemodynamic Correlations and Prognostic Implications. Heart Muscle Disease Study Group" *J Am Coll Cardiol* Sep. 22, 1993(3):808–815.

Vancheri F, Gibson D, "Relation of Third and Fourth Heart Sounds to Blood Velocity During Left Ventricular Filling", *Br Heart J* Feb. 1989;61(2):144–148.

Ishikawa M. et al, "Prognostic Significance of a Clearly Audible Fourth Heart Sound Detected a Month After an Acute Myocardial Infarction" *Am J Cardiol* Sep. 1, 1997; 80(5):619–621.

*Primary Examiner*—Scott M. Getzon
*Attorney, Agent, or Firm*—Haugen and Nikolai, P.A.

[57] ABSTRACT

An implantable monitor for collecting and storing for later telemetric readout physiologic data relating to cardiopulmonary performance. The monitor device includes an accelerometer and associated signal processing circuitry for analyzing the accelerometer output signal and deriving therefrom activity, respiratory, pulse pressure and heart sound information helpful in assessing the efficacy of therapy being rendered to the patient.

11 Claims, 3 Drawing Sheets

LONG TERM MONITORING OF ACCELERATION SIGNALS FOR OPTIMIZATION OF PACING THERAPY

BACKGROUND OF THE INVENTION

I. Field of the Invention

This invention relates generally to apparatus for long-term monitoring of the physiologic condition of a patient, and more particularly to an implantable or external device incorporating a microprocessor, a memory and an accelerometer for detecting motion due to patient activity as well as motion components relating to respiratory and cardiac rhythms, and from which critical hemodynamic diagnostic information can be derived.

II. Discussion of the Prior Art

In long term treatment of patients having cardiac abnormalities, it is important to monitor the cardiac performance over prolonged periods to assess the efficacy of any pacing or drug therapy being rendered to that patient. While so-called Holter monitors can be used to record ECG waveforms for later playback and evaluation, the amount of information that can be obtained from the ECG waveforms is necessarily limited.

It is known that data relating to the heart's mechanical functioning as a pump can be derived from heart sounds. Variability in heart sounds can provide insight into a patient's hemodynamic status. Arterial pulse pressure and various other parameters such as pre-ejection period that can be used by a physician in programming a dual chamber pacemaker for optimizing its AV delay parameter for a given patient may also be obtained from heart sounds. The timing to second heart sound may also be used to govern the rate response called for by an activity based rate responsive pacemaker. Also, heart sounds can be used to detect the occurrence of systolic and diastolic murmurs associated with valvular insufficiency or regurgitation. For example, a loud late mitral component of heart sound $S_1$ is the hallmark of hemodynamically significant mitral stenosis. When $S_1$ is loud, it is always associated with a loud opening snap, and the intensity of the snap correlates best with valve mobility. When calcification of the mitral valve occurs, the valve is stenosed and hence $S_1$ is soft, and the opening snap is absent. In addition, high frequency heart sounds detected during diastole may contain information on occluded coronary arteries. See "Accelerometer Type Cardiac Transducer for Detection of Low-Level Heart Sounds" by Padmanabhan et al., *IEE Trans Biomed Eng.*, 1993 Jan.; 40(1):21–28. It is also known that monitoring respiratory function in heart failure patients can identify patients with abnormal breathing patterns such as Cheyne-Stokes. The frequency of sleep apneas can be documented as well.

The use of movement registration for daily physical activity assessment is important to determine patient status. Standard laboratory-based exercise tests often used to define prognosis in patients with chronic heart failure do not relate to measures of normal daily activity. See Walsh JT et al., "Relation of Daily Activity Levels in Patients With Chronic Heart Failure to Long-Term Prognosis", *Am J. Cardiol*, 1997 May 15;79(10):1364–1369.

Thus, a need exists for a monitor that not only gathers and stores data over extended periods relating to the heart's electrical performance, but also its mechanical performance. In addition, there is also a need to monitor a patient's respiratory function and activity profile. It is a principal object of this invention to meet these needs.

SUMMARY OF THE INVENTION

The present invention comprises a monitor for obtaining and storing physiologic information and, in the case of an implantable monitor, comprises a moisture impervious, biocompatible housing having a plurality of ECG electrodes on an exterior surface thereof adapted to contact dermal tissue of a patient in whom the monitor is implanted. Also contained within the housing is an accelerometer for detecting mechanical vibration of the housing due to physical activity of the patient and due to heart sounds and respiratory activity. The accelerometer responds to such motions by producing an electrical signal proportional thereto.

Also incorporated into the housing is signal processing circuitry (filters) coupled to receive the electrical signals from the accelerometer and from the ECG electrodes for isolating components of the electrical signal due to physical activity, respiratory activity and heart sounds. The output of the signal processing means may be applied to an A/D converter under control of a microprocessor for converting the ECG signals and the signal components processed from the accelerometer output to digital data. Associated with the microprocessor contained within the biocompatible housing is a memory for storing the digital data at addressable locations, which data may be subsequently read out from the implanted unit to an external device via a telemetry link. Being a microprocessor-based system, it can be programmed to initiate data collection at the onset of a predefined event, either in the ECG signal, e.g., a tachyrhythmia, or in the outputs of the filters, e.g., times of high or low activity.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
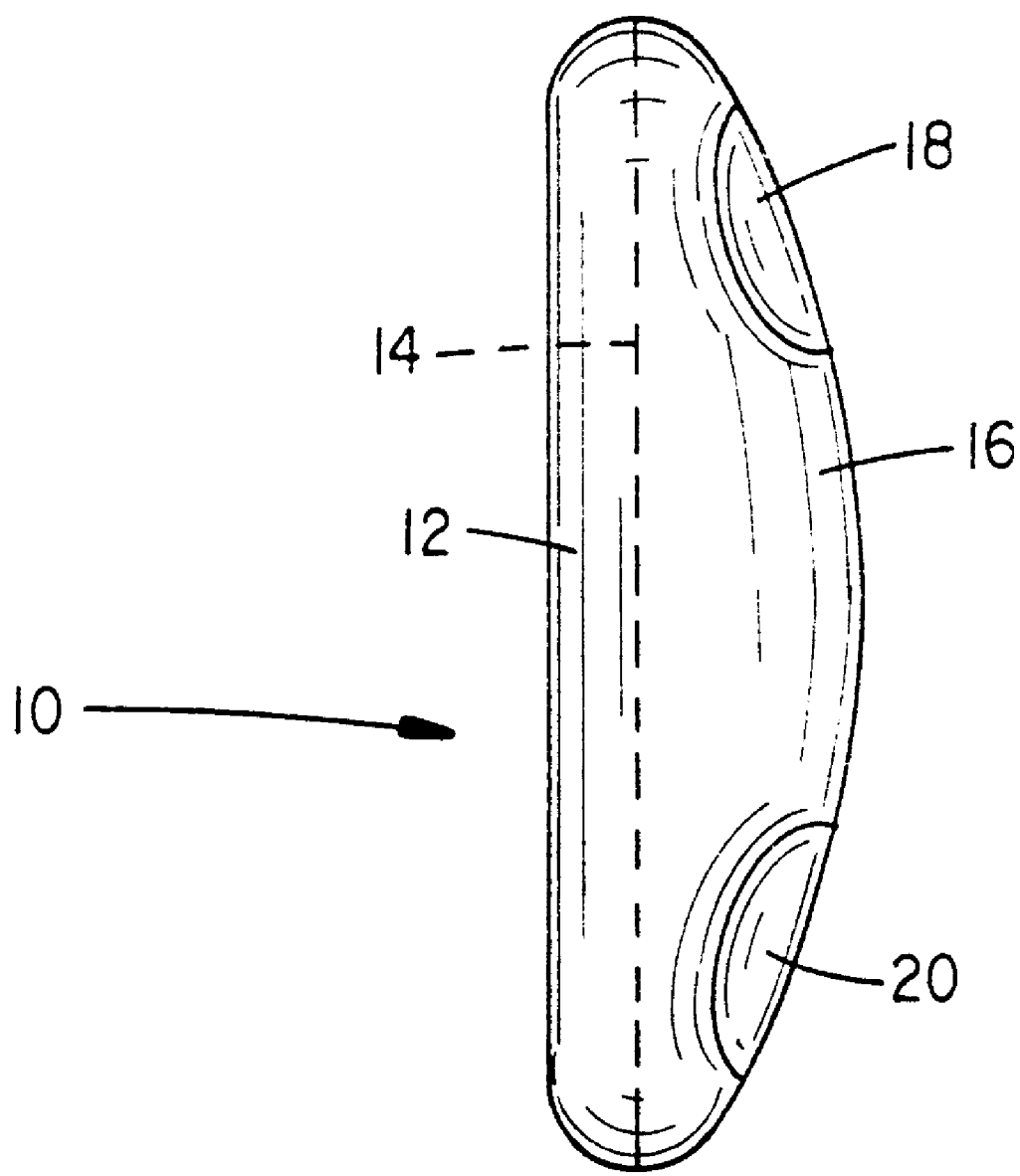
FIG. 1 is a perspective view of an implantable monitor in accordance with the present invention.

Referring to FIG. 1, there is indicated generally by numeral 10 an implantable monitor device. It includes a moisture impervious, body implantable housing 12 containing within its hollow interior a battery power supply (not shown) and electronic circuitry, which will be more particularly described. The housing 12 is preferably fabricated in two halves from thin, light-weight titanium which are then welded together along a parting line 14. The metallic housing 12 may be covered over its entire surface by a suitable insulator, such as a silastic coating 16. Bonded to the coating layer 16 so as to be insulated from the housing 12 are a plurality of electrodes, as at 18 and 20. The monitor module 10 may be surgically implanted in various locations to optimize signal-to-noise ratios. For example, to enhance mitral heart sounds, the device will ideally be implanted near the apex of the left ventricle or in the superior portion of the abdomen. To obtain better resolution of aortic heart sounds, the device may be implanted in the left or right pectoral area. It is preferably provided with a rounded contour so as not to create a noticeable bulge or cause necrosis when implanted beneath the patient's skin. The electrodes 18 and 20, thus contact subdural tissue.

Figure 2:
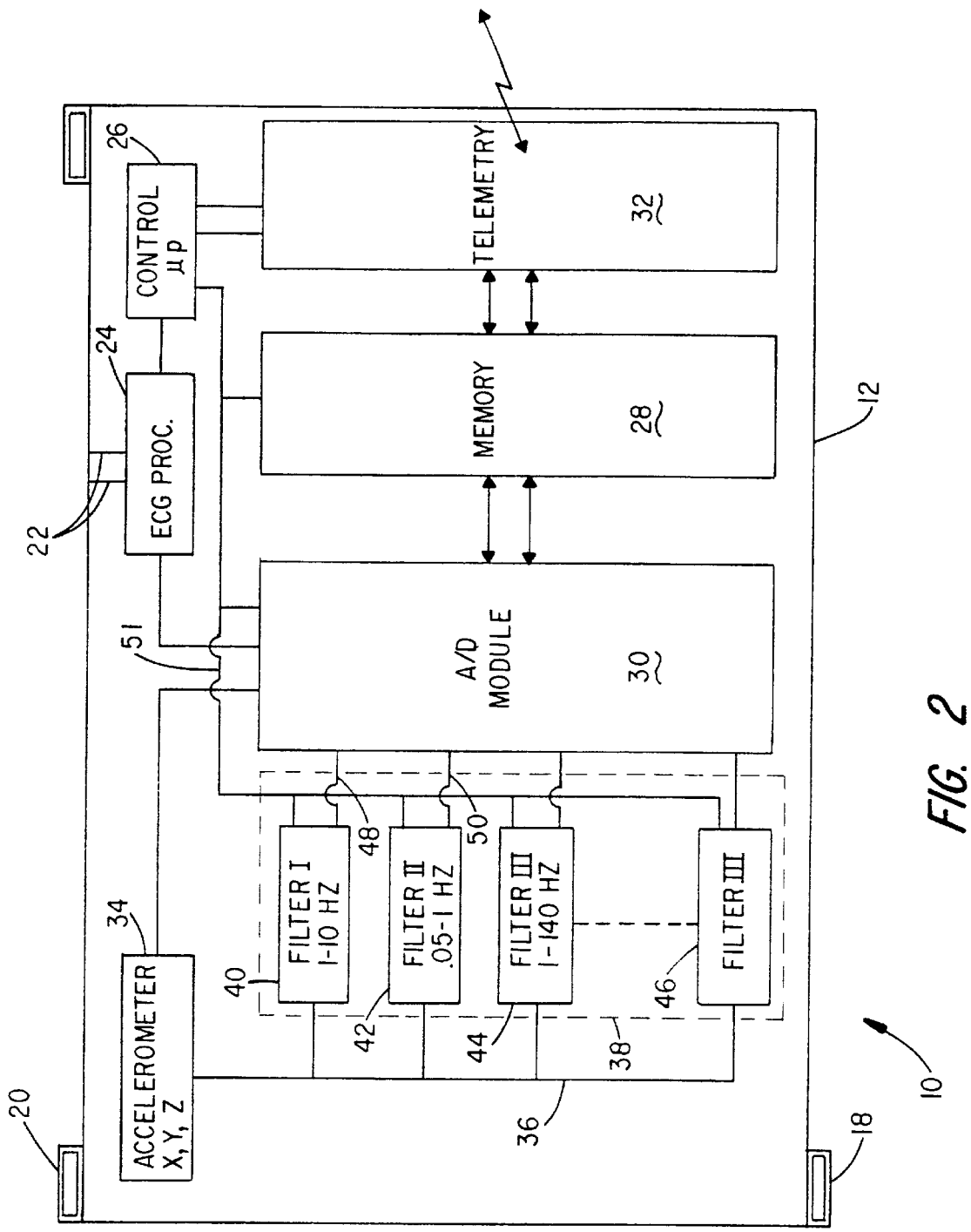
FIG. 2 is a block diagram representation of an implantable sensor monitor of the present invention.

FIG. 2 is a block diagram representation of the electronic circuitry contained within the housing 12. In FIG. 2 the housing is represented as a closed rectangle and with electrodes 18 and 20 disposed thereon. Wire feedthroughs as at 22 enter the housing through appropriate glass-to-metal seals to connect the electrodes 18 and 20 to a ECG processing module 24.

A microprocessor-based controller 26 controls the operation of the monitor device 10 and has associated with it a memory 28 in which may be stored a program of instructions executable by the microprocessor in the controller 26. The memory is also adapted to store digital information coming to it from an analog-to-digital converter module 30.

Also included within the housing 12 is a conventional telemetry link 32 that is operatively coupled to the memory 28 whereby digital information stored therein may be transmitted to a remote (external) programmer and monitor device (not shown). The telemetry device 32 is standard and is of the type commonly found in implantable cardiac rhythm management devices, such as pacemakers and defibrillators.

An accelerometer-type sensor 34 is also disposed within the housing 10 and it responds to movement and vibrations reaching it by emitting an electrical signal train on its output line 36. The accelerometer 34 may be a single axis device, but preferably is capable of sensing accelerations along three axes. The accelerometer output on line 36 is applied to signal processing circuitry shown enclosed by broken line box 38. While the signal processing circuitry may include additional amplifying and wave shaping components, the heart thereof comprises a plurality of filters 40, 42, 44 and 46. These filters are preferably bandpass filters whose upper and lower cut-off frequencies defining the pass band of each are set to isolate electrical signal components from the accelerometer output signal relating to the patient's physical activity (filter I), respiratory activity (filter II) and heart sounds (filter III).

With no limitation intended, the bandpass filter 40 may have a pass band between about 1 Hz and 10 Hz. This pass band is found to provide an output signal on line 48 relating to the patient's state of activity, such as when at rest or when engaged in exercise.

Bandpass filter 42 may have its pass band set between 0.05 Hz and 1.0 Hz which is sufficient to isolate signal artifacts in the accelerometer output due to inspiration and expiration, with the resulting signal component appearing on output line 50.

Signal components due to heart beat activity and the flow of blood through the heart can be extracted from the accelerometer output signal on line 36 by providing band pass filter 44 with a pass band that is between about 1 Hz and 140 Hz. Although choosing 1–140 Hz seems like an overlap of activity filter (1–10 Hz) in order to 3rd and 4th heart sounds, frequencies lower than 10 Hz are needed. To pick up 1st and 2nd heart sounds, especially when the patient is exercising, a 10–140 Hz bandwidth is needed. Signal components related to turbulent flow in partially occluded coronary arteries can be detected in the frequency range of 200–800 Hz.

Figure 3:
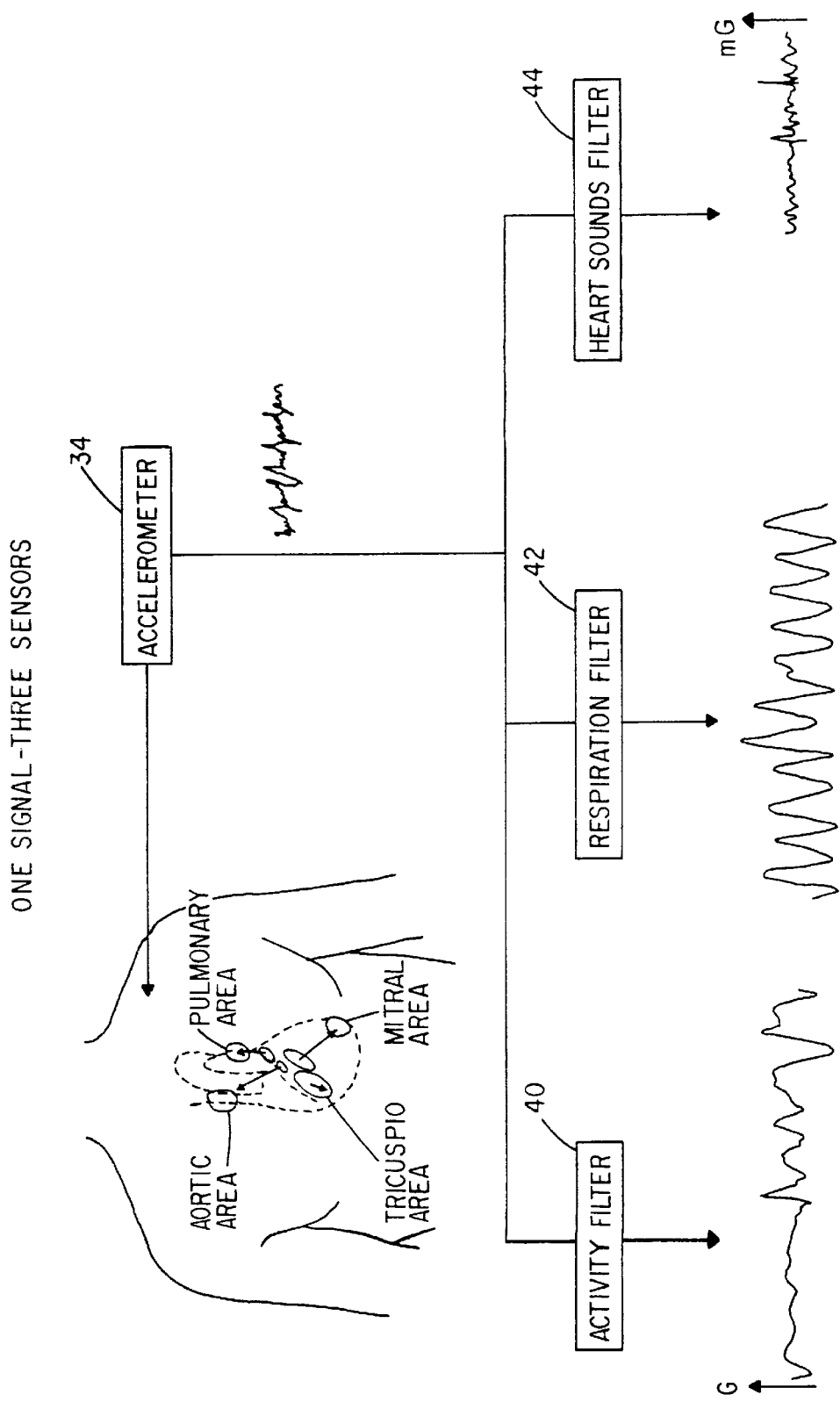
FIG. 3 illustrates the accelerometer output signal and the signal components extracted therefrom proportional to activity, respiration and systolic and diastolic heart sounds.

Referring to FIG. 3, with the monitor of the present invention implanted in the right pectoral region of the body, it is possible to derive three signal components from the accelerometer output signal. Typical waveforms of the outputs from activity filter 40, respiration filter 42 and the heart sound filters 44 are shown at the respective outputs thereof. However, high frequency heart sound due to turbulent is not shown.

A bus 51 connects the microprocessor-based controller 26 to the filter modules 40, 42, 44 and 46 allowing the filter constants to be programmed and also providing a multiplexing function whereby any one of the filter channels can be selected to apply its output to the input of the A/D module 30. Control signals on the bus 48 applied to the A/D module may also be used to program its sampling rate.

The monitor 10, in its ability to track and store patient activity and respiration signals measured by means of the accelerometer sensor 34, can be used to track patient's quality of life as well as to optimize drug or pacing therapy in patients suffering from congestive heart failure. The activity profile can also be quantified to objectively gather data for prognosis of patients with certain modes of therapy. As mentioned in the aforereferenced Walsh et al. publication, weekly measured pedometer scores have been shown to be stronger predictors of mortality compared to any parameter derived from symptom-limited exercise tests. From assessing respiratory signals, it has been shown that mortality is higher in patients with heart failure who develop Cheyne-Stokes respiration during sleep than CHF patients without Cheyne-Stokes. (See Hanly PJ, Zuberi-Khokhar NS "Increased Mortality Associated with Cheyne-Stokes Respiration in Patients With Congestive Heart Failure", *Am. J. Respir Crit Care Med,* 1996 Jan; 153(1):272–276.) The heart sound signals derived from the accelerometer can be processed to yield pulse pressure and other useful information. The third and fourth heart sounds have been determined to be related to ventricular filling, with the third heart sound corresponding to the rapid filling phase and the fourth heart sound to atrial systole. Studies have shown that the third heart sound occurs immediately after the E wave and is related to the sudden deceleration of the blood flow during passive filling of the ventricle. (See Manson AL et al., "Relationship of the Third Heart Sound to Transmitral Flow Velocity Deceleration", *Circulation* 1995 Aug 1;92(3):388–394.) It has been shown that the onset of a third heart sound during the course of evolving heart failure is coincident with the development of increased left ventricular chamber stiffness and the manifestation of rapid deceleration of early mitral inflow velocity. (See Kono T et al., "Hemodynamic Correlates of the Third Heart Sound During the Evolution of Chronic Heart Failure" *J Am Coll Cardiol* 1993 Feb 21(2):419–423.) The presence of a third heart sound has also been shown to be highly predictive of an abnormal ejection fraction, higher left ventricular filling pressure, larger left atrium and more severe mitral regurgitation. (See Patel R. et al, "Implications of an Audible Third Heart Sound in Evaluating Cardiac Function", *West J Med* 1993 Jun;158(6):606–609 and Pinamonti B et al, "Restrictive Left Ventricular Filling Pattern in Dilated Cardiomyopathy Assessed by Doppler Echocardiography: Clinical, Echocardiographic and Hemodynamic Correlations and Prognostic Implications. Heart Muscle Disease Study Group" *J Am Coll Cardiol* 1993 Sep 22(3):808–815.) Studies have revealed that fourth heart sound occurred at the onset of atrial flow and consistently before the timing of peak atrial inflow velocity. (See Vancheri F, Gibson D, "Relation of Third and Fourth Heart Sounds to Blood Velocity During Left Ventricular Filling", *Br Heart J* 1989 Feb;61(2):144–148.) A clearly audible fourth heart sound detected one month after the onset of myocardial infarction increases the risk of adverse cardiac events. (See Ishikawa M. et al, "Prognostic Significance of a Clearly Audible Fourth Heart Sound Detected a Month After an Acute Myocardial Infarction" *Am J Cardiol* 1997 Sep 1; 80(5):619–621.)

The time from onset of electrical activity to the start of ejection, namely, pre-ejection period can be derived from first heart sound. Systemic arterial pulse pressure can also be derived based on first and second heart sounds. The time to second heart sound can also be used as a rate governor to avoid higher pacing rate that can compromise the patient hemodynamically.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A monitor for obtaining and storing physiologic information comprising:
   (a) a moisture impervious, biocompatible housing having a plurality of electrodes on an exterior surface thereof contacting dermal tissue of a patient in whom the monitor is implanted for detecting ECG signals;
   (b) an accelerometer contained within said housing for detecting mechanical vibration of the housing due to physical activity of the patient and due to heart sounds, and respiratory activity and turbulent blood flow in partially occluded coronary arteries and producing an electrical signal proportional to such activity;
   (c) signal processing means coupled to receive said electrical signal for isolating components of said electrical signal due to physical activity, respiratory activity, heart sounds and turbulent blood flow in partially occluded coronary arteries;
   (d) means for converting said ECG signals and said signal components to digital data;
   (e) means coupled to the converting means for storing said digital data in a memory at addressable locations; and
   (f) means responsive to a signal applied externally of the patient's body adapted to telemeter the stored digital data to an external device.

2. The monitor as in claim 1 wherein the signal processing means includes bandpass filters tuned to isolate said signal components due to physical activity, respiration and heart sound from one another.

3. The monitor as in claim 2 wherein the bandpass filter for isolating a component of physical activity has a pass band between about 1 Hz and 10 Hz.

4. The monitor as in claim 2 wherein the bandpass filter for isolating components due to respiration has a pass band between about 0.05 Hz and 1 Hz.

5. The monitor as in claim 2 wherein the bandpass filter for isolating the component due to heart sounds has a pass band between about 1 Hz and 140 Hz.

6. The monitor as in claim 2 wherein the bandpass filter for isolating the components due to turbulent blood flow in partially occluded coronary arteries has a pass-band between about 200 Hz and 800 Hz.

7. The monitor as in claim 1 wherein upper and lower cut-off frequencies defining a pass band for the bandpass filter are programmable.

8. The monitor as in claim 1 and further including multiplexer means operatively coupled to selectively apply said signal components to the converting means.

9. The monitor as in claim 1 wherein the means coupled to the converting means for storing the digital data includes a programmed microprocessor.

10. The monitor as in claim 9 wherein the microprocessor is programmed to initiate data storage at the onset of a predetermined event detected in the ECG signal.

11. The monitor as in claim 9 wherein the microprocessor is programmed to initiate data storage at the onset of a predetermined event detected in any one of the isolated components.

* * * * *